(12) United States Patent
Pottathil

(10) Patent No.: US 11,441,145 B2
(45) Date of Patent: *Sep. 13, 2022

(54) AFFINITY MATRIX AND DEVICES FOR ISOLATION AND PURIFICATION OF RNA AND DNA FOR POINT OF CARE MOLECULAR DEVICES

(71) Applicant: AccuDx Corporation, La Jolla, CA (US)

(72) Inventor: Raveendran Pottathil, La Jolla, CA (US)

(73) Assignee: AccuDx Corporation, La Jolla, CA (US)

( * ) Notice: Subject to any disclaimer, the term of this patent is extended or adjusted under 35 U.S.C. 154(b) by 51 days.

This patent is subject to a terminal disclaimer.

(21) Appl. No.: 16/810,798

(22) Filed: Mar. 5, 2020

(65) Prior Publication Data

US 2020/0199569 A1 Jun. 25, 2020

Related U.S. Application Data

(62) Division of application No. 15/306,686, filed as application No. PCT/US2015/028374 on Apr. 29, 2015, now Pat. No. 10,597,651.

(60) Provisional application No. 61/985,998, filed on Apr. 29, 2014.

(51) Int. Cl.
| | | |
|---|---|---|
| *C12N 15/10* | (2006.01) | |
| *B01D 15/18* | (2006.01) | |
| *B01D 15/38* | (2006.01) | |
| *B01L 9/00* | (2006.01) | |
| *B01L 3/00* | (2006.01) | |

(52) U.S. Cl.
CPC ....... *C12N 15/101* (2013.01); *B01D 15/1871* (2013.01); *B01D 15/3804* (2013.01); *B01L 3/5023* (2013.01); *B01L 9/52* (2013.01); *B01L 2300/043* (2013.01); *B01L 2300/048* (2013.01); *B01L 2300/069* (2013.01); *B01L 2300/0825* (2013.01); *B01L 2400/0406* (2013.01)

(58) Field of Classification Search
CPC .................................................. C12N 15/101
See application file for complete search history.

(56) References Cited

U.S. PATENT DOCUMENTS

| | | |
|---|---|---|
| 5,234,809 A | 8/1993 | Boom |
| 5,593,835 A | 1/1997 | Rando |
| 6,511,831 B1 | 1/2003 | Bernhagen |
| 7,439,343 B2 | 10/2008 | Rege |
| 8,691,969 B2 | 4/2014 | Deggerdal |
| 2004/0152076 A1 | 8/2004 | Willson |
| 2005/0208548 A1 | 9/2005 | Block |
| 2006/0160078 A1 | 7/2006 | Cardy |
| 2008/0153078 A1 | 6/2008 | Braman |
| 2010/0216220 A1 | 8/2010 | Dawson |
| 2011/0117540 A1 | 5/2011 | Cary |

FOREIGN PATENT DOCUMENTS

| | | |
|---|---|---|
| WO | WO-199112079 | 8/1991 |
| WO | WO-1996035811 | 11/1996 |
| WO | WO-200206456 | 1/2002 |
| WO | WO-2004033720 | 4/2004 |
| WO | WO-2012002887 | 1/2012 |

OTHER PUBLICATIONS

Abramson, et al., Nucleic acid amplification technologies, Current Opinion in Biotechnology, 1993, pp. 41-47, vol. 4.1.
Grabarek, Zero-length crosslinking procedure with the use of active esters, Analytical biochemistry, 1990, pp. 131-135, vol. 185.1.
Lu, et al., Magnetic nanoparticles: synthesis, protection, functionalization, and application, Angewandte Chemie International Edition, 2007, pp. 1222-1244, vol. 46.8.
Intellectual Property Office of Singapore, Search Report and Written Opinion for SG Appln. No. 11201609008P, dated 2018, 3 pages.
Rosenthal, et al., NanoBiotechnology protocols, Humana Press, 2005, vol. 1.
Syvanen, et al., A primer-guided nucleotide incorporation assay in the genotyping of apolipoprotein E., Genomics, 1990, pp. 684-692, vol. 8.4.
Portugal et al., A New Bisintercalating Anthracycline with Picomola DNA Binding Affinity, J. Med Chem., 2005, pp. 8209-8219, vol. 48, No. 26.
United States Patent and Trademark Office, International Preliminary Report on Patentability for PCT/ PCT/US2015/028374, dated 2016, 10 pages.
United States Patent and Trademark Office, International Search Report and Written Opinion for PCT/US2015/028374, dated 2015, 14 pages.

*Primary Examiner* — Kenneth R Horlick
(74) *Attorney, Agent, or Firm* — Mintz, Levin, Cohn, Ferris, Glovsky and Popeo, P.C.

(57) ABSTRACT

The present disclosure relates to nucleic acid extraction and purification methods and devices to accomplish the same.

14 Claims, 5 Drawing Sheets

AFFINITY MATRIX AND DEVICES FOR ISOLATION AND PURIFICATION OF RNA AND DNA FOR POINT OF CARE MOLECULAR DEVICES

CROSS-REFERENCE TO OTHER APPLICATIONS

This application is a divisional of U.S. Ser. No. 15/306,686 filed Oct. 25, 2016 which is issued as U.S. Pat. No. 10,597,651 granted Mar. 24, 2020, which is a National Stage entry of PCT/US2015/028374 filed on Apr. 29, 2015, which claims priority to U.S. Provisional Application Ser. No. 61/985,998, filed Apr. 29, 2014, each of which is incorporated herein by reference in its entirety.

FIELD OF THE INVENTION

The present disclosure relates to nucleic acid extraction and purification methods and devices to accomplish the same.

BACKGROUND OF THE INVENTION

The use of DNA or RNA identification is now widely accepted as a means of distinguishing between different cells or cell types or between variants of the same cell type containing DNA mutations. Applications such as human leukocyte antigen (HLA) typing, which are more commonly carried out by identification of characteristic surface antigens using antibodies, may alternatively be affected by identification of the DNA coding for such antigens. Microbial infection or contamination may be identified by nucleic acid analysis to detect the target organism, rather than relying on detecting unique features of the cells of the microorganisms, e.g., morphological or biochemical characteristics. Genetic variations may be identified by similar means.

Molecular characterization of pathogens such as bacteria, viruses, and fungi is currently achieved by isolation from total nucleic acid, followed by cloning and subsequent analysis, or amplification of full or partial genomic sequences by polymerase chain reaction (PCR). PCR is the more powerful technique due to its ability to recover viral sequences and whole genome components from very low viral titers, and is now the preferred approach for most applications. Currently, total viral and genomic nucleic acids are isolated from infected tissues by methods which involve multi-step protocols for DNA or RNA extraction, precipitation and purification.

A frequent limitation for studying viruses and other pathogens at the molecular level is the ability to reliably obtain high quality nucleic acids from material, such as biological samples. Samples, including blood samples, must be collected and preserved in order to maintain integrity of the nucleic acids until they can be processed. This poses challenges when sample numbers are large and when working in the field. Field studies are thus constrained by the resources required for sample preservation and transportation, placing restrictions on the number of samples that can be collected in a given time and the size and remoteness of the regions that can be effectively surveyed. Timely processing and/or storage of the samples before they spoil can also be problematic in locations where access to well-equipped laboratory facilities is limited.

Biomedical engineers have traditionally developed technologies in response to the needs of the developed world's medical community. As a result, existing diagnostic systems generally meet the requirements of well-funded laboratories in highly regulated and quality-assessed environments. However, such approaches do not address the needs of the majority of the world's people who are afflicted with infectious diseases, who have, at best, access to poorly resourced health care facilities with almost no supporting clinical laboratory infrastructure. A major challenge for the biomedical engineering community is to develop diagnostic tests to meet the needs of these people, the majority of whom are in the developing world.

Nucleic acid-based diagnostics generally require an initial nucleic acid isolation step to separate the nucleic acid from materials such as protein, which may interfere in the hybridization and amplification steps. A range of methods are known for the isolation of nucleic acids, but these rely on a complex series of extraction and washing steps and are time consuming and laborious to perform.

Some embodiments of the technology described herein are based upon the identification by the applicant that a need exists for a reliable, inexpensive, quick and simple way to isolate nucleic acids from cells in mixtures or environments where they may be present at low concentrations, as a preparative first step in isolating nucleic acids from target cells in nucleic acid based cell detection procedures.

SUMMARY OF THE INVENTION

Improvements in the miniaturization of analytical technologies and the ability to assemble all steps of an assay into one portable device enhance a variety of point-of-care (POC) molecular diagnostics including probe-based assays, real-time PCR, and microarray or micropump technologies. Point of care technologies allow access to improved medical care by third-world countries and the active military. Finally, point-of-care diagnostics can help contain the emergence of new resistant strains of pathogens, encourage wellness evaluations, and reduce the overall cost of healthcare.

One bottleneck for POC diagnostics using nucleic acids is the isolation step. Classical methods for the isolation of nucleic acids from complex starting materials such as but not limited to blood, blood products, and tissues involve lysis of the biological material by a detergent or chaotrope, possibly in the presence of protein-degrading enzymes, followed by several extractions with organic solvents (e.g. phenol and/or chloroform), ethanol precipitation, centrifugation, and dialysis of the nucleic acids. Not only are such methods cumbersome and time consuming to perform, but the relatively large number of steps required increases the risk of degradation, sample loss, or cross-contamination of samples where several samples are simultaneously processed. Furthermore, these methods often require relatively large amounts of starting material (i.e., sample) in order to isolate sufficient nucleic acid to perform the diagnostic.

Improvements in methods for isolating nucleic acids are thus continually being sought, and more recently, other methods have been proposed which rely upon the use of a solid phase. U.S. Pat. No. 5,234,809, for example, discloses a method where nucleic acids are bound to a solid phase in the form of silica particles, in the presence of a chaotropic agent such as a guanidinium salt, and thereby separated from the remainder of the sample. WO 91/12079 describes a method whereby nucleic acid is trapped on the surface of a solid phase by precipitation. Generally speaking, alcohols and salts are used as precipitants. The above-mentioned publications both are incorporated herein by reference in their entireties, including for all of their methods, materials, devices, and know-how, any of which can be combined in whole or in part with the embodiments described herein. Also, the embodiments in whole or in part can be specifically excluded from one or more of the embodiments described herein.

Although such methods speed up the nucleic acid separation process, a need still exists for methods which are quick and simple to perform, enable good yields to be obtained without losses, and in particular are readily amenable to isolating nucleic acids from cells in mixtures or environments where they may be present at low concentrations, as a preparative first step in isolating nucleic acids from target cells in nucleic-acid based cell detection procedures.

The present disclosure addresses this need. In particular, whilst hybridization-based techniques such as PCR and other nucleic acid-based methods for detecting microorganisms allow high sensitivity detection of cells in samples, sample preparation (the concentration of the target cells and nucleic acid purification) can be a crucial factor for achieving the high sensitivity and reproducibility of the method.

The present disclosure proposes a novel approach to this problem wherein cell isolation and nucleic acid purification can be integrated in a single "step," by using the same solid phase for both cell adsorption and nucleic acid purification. This is achieved by binding the cells to a solid support as a first step. The same solid support is then used under conditions that lyse the bound cells, and then subsequently enable the nucleic acid to bind to the support. Methods of the present disclosure relate to the isolation of nucleic acid, and especially to a method for isolating DNA from cells, biological or environmental samples using antibiotics, which bind nucleic acids. The procedure combines an extraction step with a solid phase RNA and/or DNA isolation step. The isolation of nucleic acid is an important step in many biochemical and diagnostic procedures. For example, the separation of nucleic acids from the complex mixtures in which they are often found is frequently necessary before other studies and procedures such as but not limited to detection, cloning, sequencing, amplification, hybridization, and cDNA synthesis can be undertaken. The presence of large amounts of cellular or other contaminating material, such as but not limited to proteins or carbohydrates, in highly complex mixtures often impedes many of the reactions and techniques used in molecular biology. In addition, DNA may contaminate RNA preparations and vice versa. Thus, methods for the isolation of nucleic acids from complex mixtures such as cells and tissues are required, not only from the preparative point of view, but also in the many methods in use today which rely on the identification of DNA or RNA, such as diagnosis of microbial infections, forensic science, tissue and blood typing, and detection of genetic variations.

In one aspect, the current invention is directed to a device for isolating nucleic acid from a sample, the device comprising:

a first solid support contacting a second solid support, said first solid support comprising at least one reagent and said second solid support comprising at least one nucleic acid binding moiety;

optionally a sink contacting said second solid support; and a third solid support, wherein said third solid support is in removable contact with said second support.

In another aspect, this invention relates to a method of isolating nucleic acids from a sample, the method comprising:

contacting a first solid support with the sample;

contacting the sample with at least one reagent to disrupt the sample and release at least one target nucleic acid;

washing the first solid support with a wash buffer such that the target nucleic acid is moved to a second solid support, wherein the second solid support is in contact with the first solid support, and further wherein the second solid support comprises at least one nucleic acid binding moiety that binds the target nucleic acid;

eluting the bound target nucleic acid from the second solid support, optionally such that the target nucleic acid is moved to a third solid support, wherein the third solid support is in contact with the second solid support;

optionally eluting the target from the third solid support; and optionally detecting the eluted target nucleic acid.

In some aspects, the device comprises an affinity column. In one embodiment, the affinity column for isolating nucleic acid from a sample comprises: a solid support comprising at least one nucleic acid binding moiety.

In one non-limiting embodiment, there may be, for example, only one solid support present in the column. In one embodiment, the sample (or cells therein) is lysed before adding the lysed sample to the column. In one embodiment, a first solid support is present in the column, wherein the first solid support comprises at least one reagent. In one embodiment, the first solid support comprises one or more reagents that lyse the sample (or cells therein). In one embodiment, the first solid support comprises cell-binding moieties. In one embodiment, a second solid support is present in the column. In one embodiment, at least one solid support comprises a nucleic acid binding moiety. In one embodiment, the column further comprises a third solid support, wherein said third solid support is in removable contact with said second support. In one embodiment, the affinity column comprises multiple parts, such that at least one of the first, second and/or third solid support is not contiguous with the previous and/or next solid support. For example, in one embodiment, one or more of the solid supports is in a separate column. In one embodiment, at least one of the solid supports is a solid support matrix.

In one embodiment, the sample is a biological sample. In one embodiment, the biological sample is from a human. In one embodiment, the sample comprises a tissue sample. The tissue sample may be from any tissue, including but not limited to skin, epithelium (e.g., oral epithelium), cervix, wounded tissue, infected tissue, tumor tissue, and the like. In one embodiment, the sample comprises a bodily fluid. In one embodiment, the sample comprises a pathogen, for example bacteria, virus, or fungi. In one embodiment, the sample is an environmental sample.

In one embodiment, the at least one reagent is capable of disrupting the sample. For example, the reagent(s) may disrupt cells and/or viruses to release the target molecule(s). Reagents for disrupting samples are well-known in the art.

In one embodiment, the at least one nucleic acid binding moiety is selected from the group consisting of an antibiotic, a charged surface, and a chaotrope. In one embodiment, the at least one nucleic acid binding moiety is an intercalating compound. In one embodiment, the intercalating compound is an antibiotic.

BRIEF DESCRIPTION OF DRAWINGS

The accompanying drawing(s), which are incorporated in and constitute a part of this specification, illustrate several aspects described below.

DETAILED DESCRIPTION OF THE INVENTION

Figure 1:
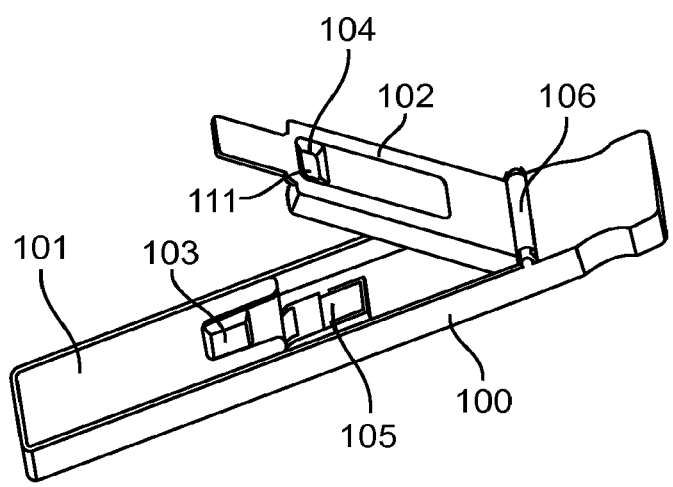
FIG. 1 shows the schematic for one embodiment of the nucleic acid isolation device.

It is to be understood that this invention is not limited to particular embodiments described, as such may, of course, vary. It is also to be understood that the terminology used herein is for the purpose of describing particular embodiments only, and is not intended to be limiting, since the scope of this invention will be limited only by the appended claims.

The detailed description of the invention is divided into various sections only for the reader's convenience and disclosure found in any section may be combined with that in another section. Unless defined otherwise, all technical and scientific terms used herein have the same meaning as commonly understood by one of ordinary skill in the art to which this invention belongs.

It must be noted that as used herein and in the appended claims, the singular forms "a", "an", and "the" include plural referents unless the context clearly dictates otherwise. Thus, for example, reference to "a compound" includes a plurality of compounds.

I. Definitions

Unless defined otherwise, all technical and scientific terms used herein have the same meaning as commonly understood by one of ordinary skill in the art to which this invention belongs. As used herein the following terms have the following meanings.

The term "about" when used before a numerical designation, e.g., temperature, time, amount, concentration, and such other, including a range, indicates approximations which may vary by (+) or (−) 10%, 5% or 1%, or any subrange or subvalue there between.

"Comprising" or "comprises" is intended to mean that the compositions and methods include the recited elements, but not excluding others. "Consisting essentially of" when used to define compositions and methods, shall mean excluding other elements of any essential significance to the combination for the stated purpose. Thus, a device or method consisting essentially of the elements as defined herein would not exclude other materials or steps that do not materially affect the basic and novel characteristic(s) of the claimed invention. "Consisting of" shall mean excluding more than trace elements of other ingredients and substantial method steps. Embodiments defined by each of these transition terms are within the scope of this invention.

The term "solid support" as used herein refers to any solid or semi-solid material. Solid supports are well-known in the art, especially with regard to chromatography. Generally, the solid support is an inert, porous solid. In some embodiments, the solid support is an active solid. Non-limiting examples of solid supports include activated alumina, powdered cellulose, silicic acid, kieselguhr, paper, glass fiber, plastic, agarose, sepharose, silica and derivatives thereof, and any other suitable solid support. Whenever the term "solid support" is used, it is envisioned that the solid support can, in some embodiments, be a solid support matrix.

The terms "affinity matrix" and "solid support matrix" as used herein refer to any matrix that allows for immobilization of a target molecule that has a given specificity for the target molecule such that the target molecule can be isolated from a sample comprising the target molecule. In one embodiment, the matrix is suitable for chromatography. The affinity matrix is described in more detail below.

The term "pad" as used herein refers to a solid support or solid support matrix.

The terms "binding moiety" and "nucleic acid binding moiety" as used herein refer to moieties within the solid support that are capable of binding nucleic acids. Binding moieties include, but are not limited to, antibiotics, as discussed in more detail below. In one embodiment, the binding moieties are bound to the solid support. In some embodiments, the nucleic acid binding moiety is a capture ligand.

The term "target molecule" as used herein refers to nucleic acids, including RNA and DNA. The target molecule may be DNA, RNA, or both. The target molecule may be a specific type of RNA, for example ribosomal RNA, transfer RNA, messenger RNA, micro RNA, small interfering RNA, viral RNA, antisense RNA, or any other type of RNA. The target molecule may be a specific type of DNA, for example genomic DNA, mitochondrial DNA, plasmid DNA, recombinant DNA, etc. The target molecule may be both RNA and DNA. In one embodiment, the nucleic acid is modified (e.g., has a tag, colorometric molecule, fluorescent molecule, other protein, or other molecule bound thereto). In one embodiment, the nucleic acid is naturally-occurring. In one embodiment, the nucleic acid is not naturally-occurring (e.g., man-made).

The terms "contacting," "in fluid contact," and "in fluid communication with" as used herein with regard to the solid supports refer to two surfaces which are in or can be brought into close proximity to one another, or that are connected via a channel, tube, capillary or other structure, such that sample, reagents, and target molecules can move from one support to the next. In one embodiment, two solid supports are adjacent and touching one another on a single piece of material, e.g., biaxially-oriented polyethylene terephthalate (BoPET; a polyester film made from stretched polyethylene terephthalate (PET) often referred to by its commercial name, Mylar). In one embodiment, one solid support is adjacent to the second solid support in an affinity column. However, in some embodiments, the solid supports are not in direct with each other. For example, in one embodiment, the solid supports are present in separate affinity columns, and the sample/reagents/molecules (flow-through) flow out of one column comprising a solid support and into the next column comprising another solid support. In some embodiments, the flow-through from one column is collected and then placed in the next affinity column.

The term "sample" as used herein refers to any sample that contains, may contain, or is believed to contain a target molecule of interest. Samples may be biological samples, environmental samples, laboratory samples, and the like. In one embodiment, the sample is a biological sample. In a preferred embodiment, the biological sample is from a human. Biological samples may comprise, without limitation, tissue samples, blood samples, external samples (e.g., swabs taken from the skin or other body part of a patient), bacterial samples, viral samples, mucous samples, samples of any bodily fluid, etc. Environmental samples include, but are not limited to, soil samples, water samples, surface samples, etc.

The term "sink" as used herein refers to any structure, such as a solid support, matrix, pad, porous material, well, and the like (e.g. that can be used to drain excess fluid from a solid support). In one embodiment, excess sample, excess reagents, unbound sample, and/or unbound molecules, and the like can flow from the solid support(s) into the sink.

Lab-on-a-chip (LOC) is a term for devices that integrate (multiple) laboratory functions on a single chip of only millimeters to a few square centimeters in size and that are capable of handling extremely small fluid volumes, down to less than picoliters. Lab-on-a-chip devices are a subset of micro-electro-mechanical systems (MEMS) devices, often called "Micro Total Analysis Systems" (μTAS).

Microfluidics is a broader term that describes also mechanical flow control devices like pumps and valves or sensors like flowmeters and viscometers. However, strictly regarded "Lab-on-a-Chip" indicates generally the scaling of single or multiple lab processes down to chip-format, whereas "μTAS" is dedicated to the integration of the total sequence of lab processes to perform chemical analysis. The term "Lab-on-a-Chip" was introduced later on when it turned out that μTAS technologies were more widely applicable than only for analysis purposes.

Microfluidics deals with the behavior, precise control and manipulation of fluids that are geometrically constrained to a small, typically sub-millimeter, scale. It is a multidisciplinary field that encompasses engineering, physics, chemistry, microtechnology and biotechnology, with practical applications to the design of systems in which such small volumes of fluids will be used. Microfluidics has emerged in the beginning of the 1980s and is used in the development of inkjet printheads, DNA chips, lab-on-a-chip technology, micro-propulsion, and micro-thermal technologies.

LOCs may provide advantages, very specifically for their applications. Typical advantages are:
  low fluid volumes consumption, because of the low internal chip volumes, which is beneficial for, e.g. environmental pollution (less waste), lower costs of expensive reagents. and less sample fluid is used for diagnostics;
  higher analysis and control speed of the chip and better efficiency due to short mixing times (short diffusion distances), fast heating (short distances, high wall surface to fluid volume ratios, small heat capacities);
  better process control because of a faster response of the system (e.g. thermal control for exothermic chemical reactions);
  compactness of the systems, due to large integration of functionality and small volumes;
  massive parallelization due to compactness, which allows high-throughput analysis;
  lower fabrication costs, allowing cost-effective disposable chips, fabricated in mass production; and
  safer platform for chemical, radioactive or biological studies because of large integration of functionality and low stored fluid volumes and energies.

Although miniaturization of amplification and detection formats have gained significant advances, few advances in sample preparation for these miniaturized devices have been made. For that specific reason, there are no simple and rapid point of care (POC) diagnostic devices for molecular biology tests.

II. Affinity Matrices and Devices of the Invention

The current invention is directed to an affinity matrix for the isolation and/or purification of nucleic acid, i.e., DNA and/or RNA. In one embodiment, the affinity matrix comprises a solid support bound to a nucleic acid binding moiety. In one embodiment, the nucleic acid binding moiety is selected from the group consisting of an antibiotic, a charged surface, an intercalating compound, and a chaotrope. In one embodiment, one or more of the listed moieties is specifically excluded from the solid support.

Solid Support or Solid Support Matrix

The solid phase may be made of glass, synthetic polymer or natural polymer. The solid support may be a column, linear strip, or flow through device.

The solid support may contain functional groups such as carboxyl, amino, aldehyde, alcohol or other reactive groups that be used to bind other large or small molecules. The binding of the functional group to the solid support or matrix may be achieved directly or through a convenient linker arm. The methods for such processes are well documented in the literature.

Some embodiments of the present invention comprise a solid phase or solid phase matrix comprised of silica/polystyrene nanocomposite particles or polystyrene latex nanoparticles bearing functional group. Nanoparticles have been extensively investigated and the effectiveness of the surface-functionalized nanoparticles, which consist of copolymers with functional molecules, is well demonstrated. The procedures for antibiotic binding to nanoparticles are also well established. For example, there are two steps for the preparation of tetracycline-modified nanoparticles. The first step is the conjugation of poly(D,L-lactide-coglycolic acid) with tetracycline via carbodiimide chemistry and is the most often employed. Three kinds of techniques—the emulsification-diffusion method, nanoprecipitation, and the dialysis method—are used for nanoparticle formation of the resulting copolymer [Methods in Molecular Biology, NanoBiotechnology Protocols, 10.1385/1-59259-901-X:121, Sandra J. Rosenthal and David W. Wright, which is incorporated herein by reference in its entirety].

The synthesis, protection, functionalization, and application of magnetic nanoparticles, as well as the magnetic properties of nanostructured systems is well documented [An-Hui Lu, E. L. Salabas, and, Ferdi Schüth, Magnetic Nanoparticles: Synthesis, Protection, Functionalization, and Application; Angew. Chem. Int. Ed. 2007, 46, 1222-1244; which is incorporated herein by reference in its entirety].

One may use micro-particles consisting of one of the several polymers as the solid phase for binding selected antibiotics. Membranes made of synthetic or natural polymers can also serve as solid phase support for binding antibiotics. In all the above cases, one or more antibiotics can be bound directly or through linker arm of varying lengths.

Device

In one aspect, the current invention is directed to a device for isolating nucleic acid from a sample, the device comprising:
  a first solid support contacting a second solid support, said first solid support comprising at least one reagent and said second solid support comprising at least one nucleic acid binding moiety;
  optionally a sink contacting said second solid support; and
  a third solid support, wherein said third solid support is in removable contact with said second support.

In one embodiment, the sample is a biological sample. In one embodiment, the biological sample is from a human. In one embodiment, the sample comprises a tissue sample. The tissue sample may be from any tissue, including but not limited to skin, epithelium (e.g., oral epithelium), cervix, wounded tissue, infected tissue, and the like. In one embodiment, the sample comprises a bodily fluid. The bodily fluid may be any bodily fluid, including but not limited to blood, mucous, serum, sputum, saliva, gastric juice, gastric acid, bile, urine, breast milk, amniotic fluid, cerebrospinal fluid, cerumen, feces, lymph, endolymph, perilymph, pericardial fluid, peritoneal fluid, pus, synovial fluid, semen, tears, sweat, rheum, vomit, and the like.

In one embodiment, the sample comprises a pathogen. In one embodiment, the sample comprises one or more bacteria and/or nucleic acids from bacteria. In one embodiment, the sample comprises one or more viruses and/or nucleic acids from virus. In one embodiment, the sample comprises one or more fungi and/or nucleic acids from fungi. In one embodiment, the sample is an environmental sample.

In one embodiment, the at least one reagent is capable of disrupting the sample. For example, the reagent(s) may disrupt cells and/or viruses to release the target molecule(s). Reagents for disrupting samples are well-known in the art.

In one embodiment, the at least one nucleic acid binding moiety is selected from the group consisting of an antibiotic, a charged surface, and a chaotrope. In one embodiment, the at least one nucleic acid binding moiety is an intercalating compound. In one embodiment, the intercalating compound is an antibiotic.

Antibiotics and other nucleic acid binding moieties are discussed in more detail in the "Capture Ligands" section, below.

In one embodiment, the third solid support can be removed from the device for further processing of the target molecules.

In one embodiment, the solid support is part of a device similar to that depicted in FIG. 1. In some embodiments, the device comprises a housing 100 for holding a strip 105 comprising one or more solid support matrices. Said solid support matrices may be in physical contact with one another.

The device optionally comprises a first cover 101 to protect the strip 105 from damage, contamination, and the like. The cover 101 covers at least a portion of the housing 100 and at least a portion of the strip 105. The cover optionally includes at least one window 103 for application of a sample to the pad(s) of strip 105 and/or through which a separate pad 111 can be contacted to the pad(s) of strip 105.

The device optionally comprises a second cover 102. The second cover 102 may be hingedly and/or removably attached to the housing 100. For example, hinge 106 can be configured such that cover 102 can be removed from the housing 100, for example for later processing of the target molecules bound to pad 111. The second cover holds at least one pad 111, wherein pad 111 comprises a solid support. The second cover 102 optionally contains one or more windows 104 such that pad 111 can be viewed and/or accessed through the window 104.

Figure 2:
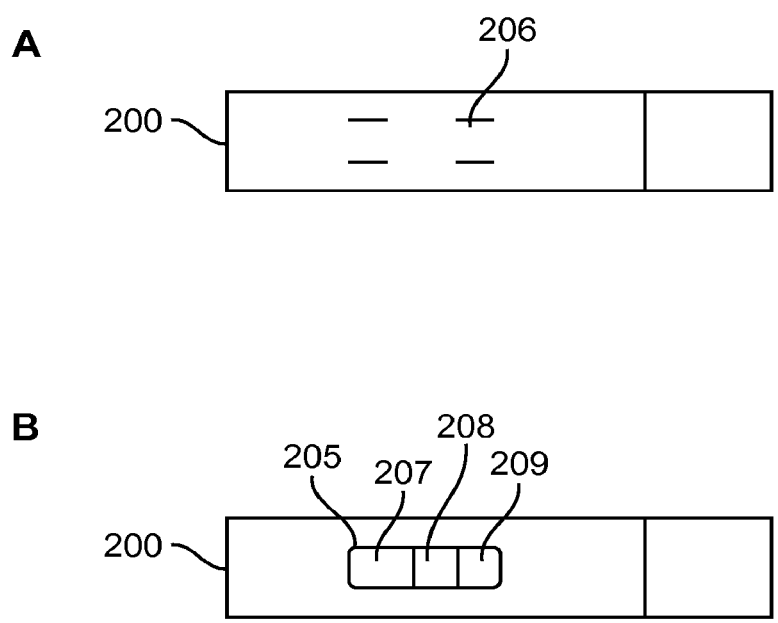
FIG. 2 shows an embodiment of the nucleic acid isolation device.

In one embodiment, the solid support is part of a device similar to that depicted in FIG. 2. A housing 200 optionally comprises a holder 206 for a strip 205 comprising at least one pad 207 and/or 208. When present in housing 200, the holder 206 holds the strip 205 in place. When two or more pads 207 and 208 are used, the pads are adjacent to one another such that a sample and/or target molecules can move between the pads, for example by capillary action. In one embodiment, no additional reagents are required to move the sample and/or target molecules between the pads 207 and 208. In one embodiment, one or more reagents (e.g., buffer) are added to at least one pad 207 or 208 to move the sample and/or target molecules between the pads 207 or 208. In one embodiment, the strip 205 further comprises a well or sink 209. In one embodiment, the well or sink 209 is part of the housing 200 rather than the strip 205. In one embodiment, the well or sink 209 is a pad.

Figure 3:
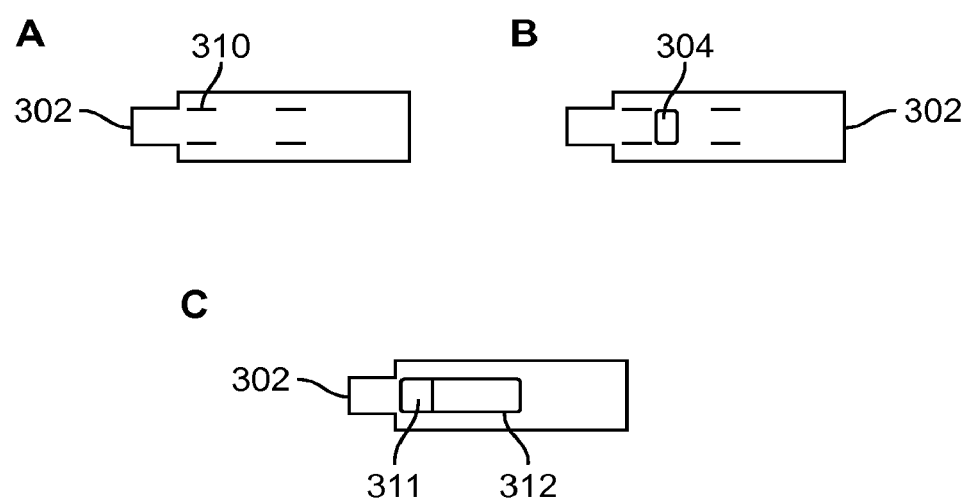
FIG. 3 shows an embodiment of the nucleic acid isolation device.

In one embodiment, the solid support is part of a device similar to that depicted in FIG. 3. A housing 302 optionally comprises a holder 310 for a strip 312 comprising at least one pad 311. The housing 302 optionally comprises at least one window 304 such that pad 311 can be viewed and/or accessed through the window 304.

Figure 4:
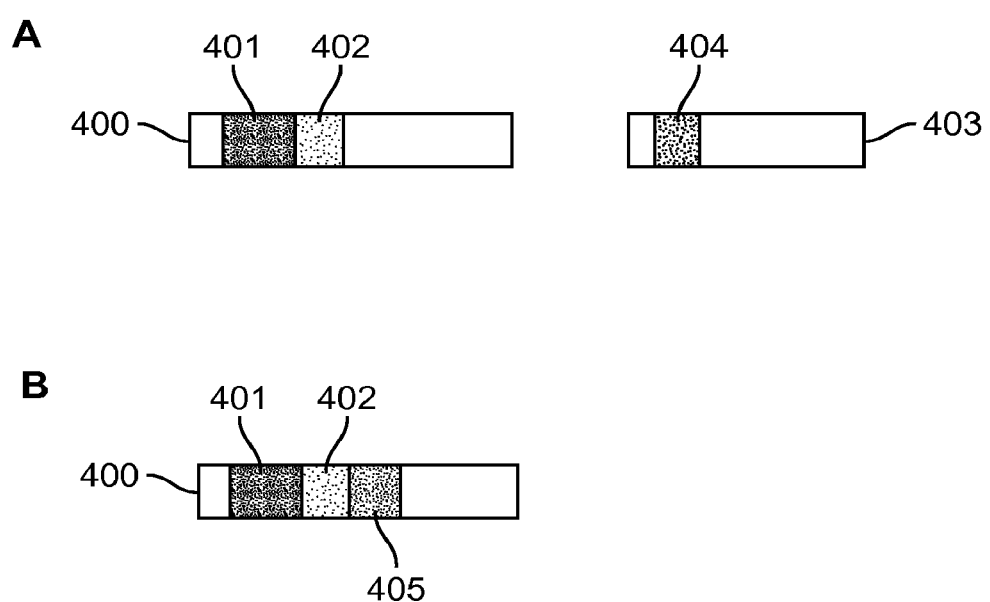
FIG. 4 shows an embodiment of the nucleic acid isolation device.

In one embodiment, the solid support is in the form of one or more strips as depicted in FIG. 4. Strip 400 comprises at least one pad 401 and/or 402. When two or more pads 401 and 402 are used, the pads are adjacent to one another such that a sample can move between the pads 401 and 402, for example by capillary action. In one embodiment, no additional reagents are required to move the sample and/or target molecules between the pads 401 and 402. In one embodiment, one or more reagents (e.g., buffer) are added to at least one pad 401 or 402 to move the sample and/or target molecules between the pads 401 or 402. In one embodiment, the strip 400 further comprises a well or sink 405. In one embodiment, the well or sink 405 is a pad.

In some embodiments, pad 404 is located on strip 400 adjacent to pad 402, such that the sample and/or target molecule can move from pad 402 into pad 404, for example via capillary action. In a preferred embodiment, pad 404 is located on a separate strip 403. Pad 404 can be contacted to pad 402 and/or pad 401 at a predetermined time during the method, as described in more detail below.

The strips (e.g., 105, 205, 312, 400 and/or 403) may be comprised of any suitable material. Suitable materials include materials that can be made thin enough to fit in the housing, are amenable to attachment with the pads, and are resistant to the reagents and samples that are added/to be added onto the device. In an preferred embodiment, the material is non-reactive, particularly with the target molecules. Non-limiting examples include BoPET/Mylar, nitrocellulose, polyvinylidene fluoride, other plastics, and the like.

In some embodiments, the device comprises an affinity column. In one embodiment, the affinity column for isolating nucleic acid from a sample comprises:

a first solid support contacting a second solid support, said first solid support comprising at least one reagent and said second solid support comprising at least one nucleic acid binding moiety; and a third solid support, wherein said third solid support is in removable contact with said second support.

In one embodiment, the affinity column comprises multiple parts, such that at least one of the first, second and/or third solid support is not contiguous with the previous and/or next solid support. For example, in one embodiment, one or more of the supports is in a separate column. In one embodiment, a sink or other material is inserted between the first and second and/or second and third supports.

In one embodiment, the first solid support comprises one or more reagents that disrupt a sample to release target molecules. For example, the reagent(s) may lyse cells (e.g., bacterial cells, red blood cells, tissue cells, and the like) to release DNA and/or RNA. In one embodiment, the first solid support comprises molecules that, when mixed with water, form a buffer (e.g. a lysis buffer).

In one embodiment, the second solid support comprises a nucleic acid affinity matrix. The nucleic acid affinity matrix comprises the nucleic acid binding moiety. In some embodiments, the nucleic acid binding moiety is a capture ligand. In one embodiment, the at least one nucleic acid binding moiety is selected from the group consisting of an antibiotic, a charged surface, and a chaotrope. In one embodiment, the at least one nucleic acid binding moiety is an intercalating compound. In one embodiment, the intercalating compound is an antibiotic. Antibiotics and other nucleic acid binding moieties are discussed in more detail in the "Capture Ligands" section, below.

In one embodiment, a sink is adjacent to one or more solid support matrices for collecting unbound sample material. In one embodiment, the sink is a well. In one embodiment, the sink is a solid support or other type of porous material.

In one embodiment, the third solid support comprises a porous solid phase material. In one embodiment, the third solid support comprises an elution buffer. Elution buffers for nucleic acids are well-known in the art and include, without limitation, acids, bases, acetonitrile, methanol, use low salt buffers, water, free antibiotics, and chaotropes. In one embodiment, the third solid support comprises molecules that, when mixed with water, form an elution buffer.

The solid support or solid support matrix can be any suitable material, including those known in the art, for preparing columns and/or chromatography devices. In one embodiment, one or more of the solid supports comprises paper, glass fiber, and/or plastic. In one embodiment, one or more of the solid supports comprises agarose, sepharose, magnetic beads, and the like. The solid support is described in more detail below. In one embodiment, one or more of the solid supports comprises molecules that, when mixed with water, form a buffer. The buffer may be any suitable buffer, including (without limitation)

In one embodiment, one or more solid supports comprise at least one enzyme, including, without limitation, a nuclease (e.g. DNase, RNase), a proteinase, and the like. In one embodiment, one or more solid supports comprise at least one nucleic acid stabilizing molecule. Nucleic acid stabilizing molecules include, without limitation, nuclease inhibitors.

In one embodiment, the third solid support is capable of being separated from the device. This may be beneficial, for example, in order to enable transport, storage, and/or later (in time) target molecule detection.

In some embodiments, one or more solid supports comprise at least one molecule that enables visual detection of the target molecules. Such visual detection molecules are well-known in the art. Non-limiting examples include the presence of a fluorophore, chromophore, or colorimetric molecules and/or enzymes (e.g., streptavidin/avidin, horseradish peroxidase, and the like). The molecule(s) for visual detection can be attached to the target molecule during the isolation process, for example by attaching the molecule(s) for visual detection to the capture ligand or another moiety that binds the target molecule (e.g., single-stranded nucleic acid, RNA- or DNA-binding proteins, nanoparticles, and the like). Alternatively, the molecule(s) for visual detection can be attached directly to the target molecule (e.g. by covalent bond) at any step of the isolation procedure (e.g. when the target molecule is bound to the nucleic acid binding moiety).

Capture Ligands

The nucleic acid binding moiety can be any molecule or moiety that is capable of binding nucleic acids. In one embodiment, the nucleic acid binding moiety is an intercalating compound. In one embodiment, the nucleic acid binding moiety is an antibiotic. In one embodiment, the nucleic acid binding moiety is a chaotrope. In one embodiment, the nucleic acid binding moiety is a nucleic acid-binding solid phase. In one embodiment, the nucleic acid binding moiety comprises silica particles. In one embodiment, the nucleic acid binding moiety is a solid support having a charged surface. In one embodiment, the nucleic acid binding moiety is a support coated with polyamines. In one embodiment, the nucleic acid binding moiety comprises a complementary DNA or RNA sequence. In one embodiment, the nucleic acid binding moiety comprises DNA or RNA binding proteins. In one embodiment, the nucleic acid binding moiety comprises viral proteins capable of binding to viral nucleic acid.

In one embodiment, the nucleic acid binding moiety is attached to the solid support immediately prior to use (e.g. by the end user). Thus, the solid support can be amenable to binding by the nucleic acid binding moiety (e.g. a surface of the solid support comprises an active moiety or can be activated so as to covalently or otherwise bind the nucleic acid binding moiety to the surface).

In one aspect of the invention, the nucleic acid binding moiety is an intercalating agent, including antibiotics, anticancer compounds and the like. Non-limiting examples include peptide and small molecule antibiotics and anticancer compounds that intercalate with nucleic acids, as well as other chemical entities that are capable of intercalating with nucleic acid sequences. Several non-limiting examples are anthracyclines such as Daunorubicin, Doxorubicin, Epirubicin and Idarubicin, and peptide antibiotics such as Echinomycin, and any other like compound or moiety.

WP631 ($C_{62}H_{64}N_2O_{20} \cdot C_2H_8S_2O_6$; Molecular Weight: 1349 (anhydrous)) is a fluorescent bisintercalating anthracycline antibiotic shown to have activity against multi-drug-resistant cancer cells. It is composed of two monomeric units of daunorubicin, symmetrically linked together via p-xylenyl 3-NH2 sites Embodiments of the present invention comprise capture ligands comprising DNA- and RNA-binding molecules selected from various antibiotic classes. Suitable antibiotic classes such as aminoglycosides, ansamycins, carbacephem, carbapenems, glycopeptides, and macrolides.

Aminoglycosides are among the most commonly used broad-spectrum antibiotics in the anti-infective armamentarium. The vast majority of aminoglycosides are bactericidal, have predictable pharmacokinetics, and often act in synergy with other antibiotics. These properties make them valuable as anti-infectives.

Aminoglycosides are multifunctional hydrophilic sugars that possess several amino and hydroxy functionalities. The amine moieties are mostly protonated in biological media; hence, these antibiotics can be considered polycationic species for the purpose of understanding their biological interactions. Since they are polycationic, they show a binding affinity for nucleic acids.

Selected antibiotics from the glycopeptide group such as vacomycin, teicoplanin and televancin may be used as RNA capture molecules. Selected antibiotics from classes of tetracyclins may be used as capture ligand for RNAs. Examples include doxycycline, minocycline, oxytetracycin and tertracyclin. Quinilone and their derivataives may be used as capture ligand for single-stranded nucleic acids. Examples include ciprofloxacin, enoxacin, levofloxacin, lomifloxaxacin, moxifloxacin and norfloxacin. Various compounds selected from antibiotics of the sulfonamide class may be used as solid-phase capture ligands. Examples include but are not limited to sufacetamide, suladiazine, sulfmethizole, trimethoprim and mafinide.

The capture ligand may be selected from antibiotic classes such as Aminoglycosides, Ansamycins, Cephalosporins, Glycopeptides, Marcolids, Quinolones, Sulfonamides, Tetracyclins, etc. Additional classes include Arsphenamine, Chloramphenicol, Clindamycin, Lincomycin, Ethambutol, Fosfomycin, Fusidic acid, Furazolidone, Isoniazid, Linezolid, Metronidazole, Mupirocin, Nitrofurantoin, Platensimycin, Pyrazinamide, Quiupristin, Rifampicine, thiamphenicol, Tinidazole, Dapsone, Clofazimine, and the like.

The following antibiotics are known to bind nucleic acids (available from Sigma Aldrich):

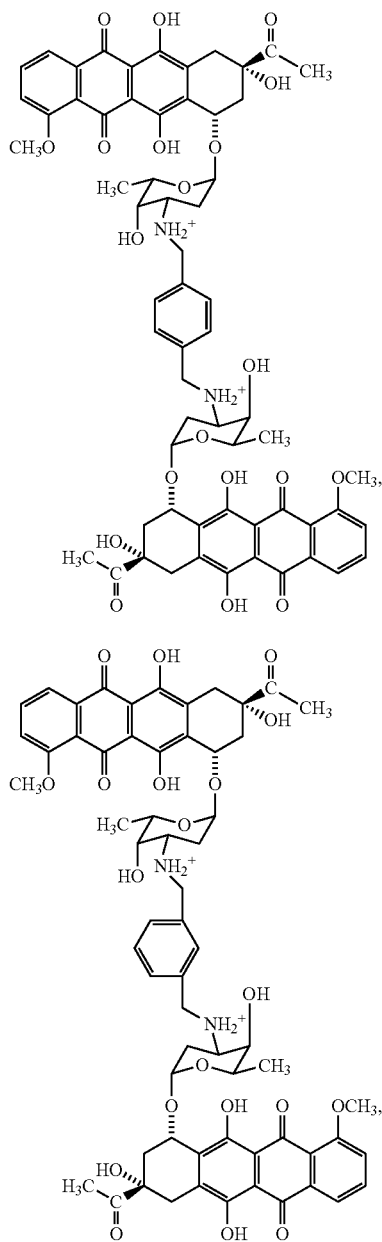

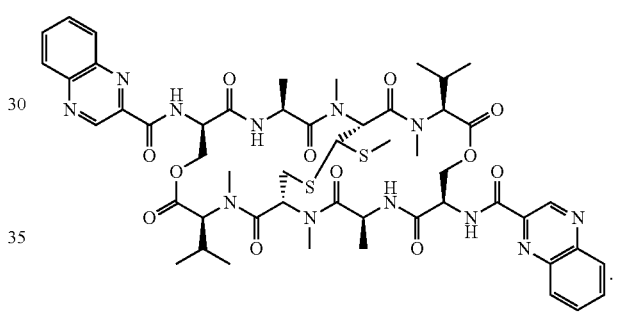

Daunorubicin

WP631, WP762, and daunorubicin; Echinomycin ($C_{51}H_{64}N_{12}O_{12}S_2$; N,N'-(2,4,12,15,17,25-hexamethyl-11, 24-bis(1-methylethyl)-27-(methylthio)-3,6,10,13,16,19,23, 26-octaoxo-9,22-dioxa-28-thia-2,5,12,15,18,25-hexaazabicyclo(12.12.3)nonacosane-7,20-diyl)bis(2-quinoxalinecarboxamide), Quinomycin A; a peptide antibiotic that intercalates into DNA; available from Sigma Aldrich):

Alternative non-specific nucleic acid-binding techniques include the use of detergents as described in WO 96/18731 of Dynal AS (the so-called "DNA Direct" procedure), which is incorporated herein by reference in its entirety, and the use of chaotropes and a nucleic acid-binding solid phase such as silica particles. Ionic binding of the nucleic acid to the support may be achieved by using a solid support having a charged surface, for example a support coated with polyamines.

Likewise, the support may comprise binding partners to assist in the selective capture of nucleic acids. For example, complementary DNA or RNA sequences, DNA binding proteins, or viral proteins binding to viral nucleic acid. The attachment of such proteins to the solid support may be achieved using techniques well known in the art.

In one embodiment, at least one class of antibiotic is specifically excluded from the invention. In one embodiment, at least one antibiotic from at least one class of antibiotics is specifically excluded from the invention. In one embodiment, at least one type of nucleic acid binding moiety is specifically excluded from the invention.

In one embodiment, this disclosure relates to any detection or purification of a nucleic acid from a sample comprising using an antibiotic as a capture moiety. Thus, it is contemplated that any device or structure, including but not limited to, those described herein, may be used in methods that utilize an antibiotic as a capture moiety for a nucleic acid.

Kits

In one embodiment, the various reactants and components required to perform the methods of the invention are conveniently supplied in kit form. Such kits represent a further aspect of the invention.

In one embodiment, nucleic acid extraction cartridges of the present invention are based on a novel capture ligand mixture that consists of a solid phase bound with a mixture of known antibiotic. These compounds are selected based on their affinity to DNA and/or RNA.

Embodiments of the present invention provide a kit for isolating nucleic acid from a sample comprising:
(a) a solid support;
(b) optionally, means for binding cells to said solid support;
(c) means for lysing said cells and removing proteins; and
(d) means for binding nucleic acid to the solid support.

The various means (b), (c) and (d) may be as described and discussed above, in relation to the method of the invention.

Optionally further included in such a kit may be instructions for use of the device in a readable medium.

The term "readable medium" as used herein refers to a representation of data that can be read, for example, by a human or by a machine. Non-limiting examples of human-readable formats include pamphlets, inserts, or other written forms. Non-limiting examples of machine-readable formats include any mechanism that provides (i.e., stores and/or transmits) information in a form readable by a machine (e.g., a computer, tablet, and/or smartphone). For example, a machine-readable medium includes read-only memory (ROM); random access memory (RAM); magnetic disk storage media; optical storage media; and flash memory devices. In one embodiment, the machine-readable medium is a CD-ROM. In one embodiment, the machine-readable medium is a USB drive. In one embodiment, the machine-readable medium is a Quick Response Code (QR Code) or other matrix barcode.

Optionally further included in such a kit may be buffers, reagents for making buffers, salts, polymers, enzymes, etc.

Optionally, the kit includes one or more nucleic acid binding moieties. Such one or more nucleic acid binding moieties may be provided in any form, e.g. separately in a form that allows the moiety to be bound to a solid support by and end user; pre-bound to a solid support. In one embodiment, multiple nucleic acid binding moieties are provided such that an end user can choose which moiety to use for a given application. In one embodiment, the multiple nucleic acid binding moieties are provided as multiple solid supports. In one embodiment, one or more solid supports in the device, affinity column, or affinity matrix as described herein is removable such that the end user can choose the solid support to be used for a given application.

The embodiments described herein are further described in conjunction with the methods of the invention, below.

III. Methods of the Invention

The present invention comprises a method of isolating nucleic acid molecules using nucleic acid binding moieties, e.g. antibiotic compounds, as ligands.

In one embodiment, the methods of the present invention are directed to nucleic acid isolation comprising the steps of: 1) contacting a solid support with a sample wherein the solid support comprises cell binding moieties and wherein the sample comprises a target molecule; 2) allowing the cells to bind to the solid support; 3) washing the solid support to remove non-bound moieties; and 4) binding the target molecule to a separate solid support comprising a nucleic acid binding moiety. In a preferred embodiment, the nucleic acid binding moiety is an antibiotic.

In one embodiment, isolation and purification of nucleic acids from samples comprises the following steps:
a) Contacting the samples to a solid phase loaded with a reagent that disrupts the sample to release target molecules;
b) Washing the solid phase with a wash buffer to move released target molecules to another solid support with nucleic acid biding moieties that bind the target molecules and to move unbound sample and target molecules to a separate sink area;
c) Eluting the bound target molecules with a suitable release buffer to release target molecules, optionally to a separate solid support; and
d) Optionally detecting the eluted nucleic acid.

In one embodiment, this invention relates to a method of isolating nucleic acids from a sample, the method comprising:
contacting a first solid support with the sample;
contacting the sample with at least one reagent to disrupt the sample and release at least one target nucleic acid;
washing the first solid support with a wash buffer such that the target nucleic acid is moved to a second solid support, wherein the second solid support is in contact with the first solid support, and further wherein the second solid support comprises at least one nucleic acid binding moiety that binds the target nucleic acid; and
eluting the bound target nucleic acid from the second solid support, such that the target nucleic acid is moved out of the second solid support, said target optionally moved to a third solid support, wherein the third solid support is in contact with the second solid support.

In one embodiment, the eluted target nucleic acid is detected. Detection may be by any means known in the art and/or described herein.

In some embodiments, samples comprising target molecules include but are not limited to whole blood. In some embodiments, samples are contacted to a first area or zone of the solid phase (i.e., the first solid support).

In one embodiment, the sample is a biological sample. In one embodiment, the biological sample is from a human. In one embodiment, the sample comprises a tissue sample. The tissue sample may be from any tissue, including but not limited to skin, epithelium (e.g., oral epithelium), cervix, wounded tissue, infected tissue, tumor, suspected tumor (e.g. biopsy), and the like. In one embodiment, the sample comprises a bodily fluid. The bodily fluid may be any bodily fluid, including but not limited to blood, mucous, serum, sputum, saliva, gastric juice, gastric acid, bile, urine, breast milk, amniotic fluid, cerebrospinal fluid, cerumen, feces, lymph, endolymph, perilymph, pericardial fluid, peritoneal fluid, pus, synovial fluid, semen, tears, sweat, rheum, vomit, and the like.

In one embodiment, the sample comprises one or more bacteria and/or nucleic acids from bacteria. In one embodiment, the sample comprises one or more viruses and/or nucleic acids from virus. In one embodiment, the sample is an environmental sample.

In one embodiment, the at least one reagent is capable of disrupting the sample. For example, the reagent(s) may disrupt cells and/or viruses to release the target molecule(s). Reagents for disrupting samples are well-known in the art.

In one embodiment, the at least one nucleic acid binding moiety is selected from the group consisting of an antibiotic, a charged surface, and a chaotrope. In one embodiment, the at least one nucleic acid binding moiety is an intercalating compound. In one embodiment, the intercalating compound is an antibiotic.

Various embodiments of the solid support are detailed in the "Affinity matrices and devices of the invention" above.

In some embodiments, the first solid support comprises reagents capable of disrupting the sample and releasing target molecules. In one embodiment, the first solid support comprises red blood cell retention reagents such as thrombin, lectin, and the like. This is referred to as a blood separation zone. In one embodiment, the first solid support comprises one or more cell binding moieties bound to the solid support. In one embodiment, the first solid support comprises one or more virus binding moieties bound to the solid support.

In one embodiment, contiguous to the first solid support is another zone or pad (second solid support) containing a nucleic acid affinity matrix comprising at least one nucleic acid binding moiety. Nucleic acid binding moieties include, but are not limited to, antibiotics, intercalating compounds, charged surface, and chaotropes. Examples of antibiotics include but are not limited to the following antibiotic classes: aminoglycosides such as amikacin, gentamycin, kanamycin, neomycin, streptomycin, tobramycin, and paraomycin. Antibiotics serve as capture ligands as they are capable of binding target molecules such as DNA and RNA. These compounds may be used singly or in combination on the solid support.

In one embodiment, after the sample is contacted to the first solid support, the cells are disrupted and target molecules move into the second solid support, e.g. by capillary action. In one embodiment, the target molecules bind the antibiotics in the second solid support, forming a target-antibiotic complex.

In one embodiment, a cavity, area, or porous material next to the second solid support constitutes a sink for collecting unbound sample material. In one embodiment, the unbound material moves into the sink. In one embodiment, the unbound material moves into the sink by capillary action.

In one embodiment, wash buffer is optionally added to at least one solid support. Wash buffer may comprise organic or inorganic buffers at molarities between 0.5 and 5 M of various salts including metal chlorides. In one embodiment, hydrogen ion concentration is be maintained at pH between 3 and 11 with or without metal ions such as calcium, magnesium, copper, iron, etc. In one embodiment, the wash buffer moves unbound material via capillary action to the sink zone. In one embodiment, the wash buffer comprises high salt, such as greater than or equal to 1M NaCl in phosphate buffered saline. In one embodiment, excess wash buffer moves into the sink.

In one embodiment, at least a portion of the target molecules bound to the second solid support move into the third solid support upon contacting of the second solid support with the third solid support. In one embodiment, the third solid support comprises an elution buffer. In one embodiment, the third solid support comprises at least one molecule that is capable of forming an elution buffer upon contact of the third solid support with water or an aqueous solution. In one embodiment, water, aqueous solution, or elution buffer is added to the first and/or second and/or third solid support. In one embodiment, water, aqueous solution, or elution buffer is added to the first and/or second and/or third solid support before contacting of the second solid support with the third solid support. In one embodiment, water, aqueous solution, or elution buffer is added to the first and/or second and/or third solid support after contacting of the second solid support with the third solid support. The target molecules (e.g., nucleic acids) can move into the third solid support by any method.

Elution buffer may consist of low molarities buffers with or without the above-mentioned antibiotics. In one embodiment, the molarity of elution buffer comprises between 0.001 and 0.1 M salt, such as, without limitation, ammonium sulphate or PBS with or without 0.1 to 1 M free antibiotics that are used in the solid support.

In one embodiment, elution buffer separates or releases the target molecule from the target molecule-antibiotic complex. In one embodiment, the target molecules are captured by contacting a third solid support to the second solid support. In one embodiment, the third solid support comprises a known size and area of porous solid phase material. In one embodiment, the third solid support contains nucleic acid stabilizing molecules, such as but not limited to nuclease inhibitors.

In one embodiment, the third solid support is capable of being separated from the device in order to enable transport and later (in time) target molecule detection. In one embodiment, nucleic acid detection may be chosen from one of the various established methods including electrophoresis, direct hybridization before or after nucleic acid amplification, or visualization (e.g., colorimetric, fluorophore, and the like).

In one embodiment, sample is added to the first solid support, which has reagents that release target (nucleic acid) molecules from a sample. In one embodiment, the released target moves by capillary action to the second solid support which comprises nucleic acid-binding antibiotics. In one embodiment, the antibiotics are bound to the solid support such that they are immobilized. In one embodiment, the antibiotic binds to the target molecule and immobilizes the target to the solid support. In one embodiment, wash buffer is added to move unbound material into the sink. In one embodiment, the elution buffer is added (e.g., buffer comprising components that dislodge the target from being bound to the antibiotics). In one embodiment, the second solid support is contacted to a third solid support. In one embodiment, such contacting occurs by closing a cover that has the third solid support attached thereto over a housing that has the second solid support attached thereto, such that the third solid support contacts the second solid support.

In general, DNA or RNA is identified by hybridization to one or more oligonucleotides under conditions of stringency sufficient to ensure a low level of non-specific binding. Commonly, the hybridizing nucleotides are used in pairs as primers in the various forms of in vitro amplification, primarily polymerase chain reaction (PCR), but also Ligase Amplification Reaction (LAR), Self-Sustained Sequence Replication (3SR) and Q-beta replicase amplification system. Following amplification, the DNA may be further characterized by sequencing, e.g. by the Sanger method. In some instances, amplification and sequencing steps may be combined.

In one embodiment, the nucleic acid is precipitated by adding a precipitant, e.g. alcohol, to the mixture containing the support and lysed cells. Thus, an appropriate volume of alcohol, e.g. 100% or 96% ethanol, may simply be added to the mixture, and incubated for a time period sufficient to allow the released nucleic acid to become bound to the support.

Optionally, embodiments of the present method include one or more wash steps, following the nucleic acid binding step. Any conventional washing buffers or other media may be used. Generally speaking, low to moderate ionic strength buffers are preferred, e.g. 10 mM Tris-HCl at pH 8.0/10 mM NaCl. Other standard washing media may also be used such as 70% ethanol.

In one embodiment, following the nucleic acid isolation process and any optional washing steps which may be desired, the support carrying the bound nucleic acid is transferred e.g. resuspended or immersed into any suitable medium such as but not limited to water or low ionic strength buffer. Depending on the support and the nature of any subsequent processing desired, it may or may not be desirable to release the nucleic acid from the support. In one embodiment, the support carrying the bound nucleic acid is removable from a device or affinity column as described herein.

In the case of a particulate solid support such as magnetic or non-magnetic beads, this may be used directly, for example in PCR or other amplifications, without eluting the nucleic acid from the support. Also, for many DNA detection or identification methods, elution is not necessary since, although the DNA may be randomly in contact with the bead surface and bound at a number of points by hydrogen bonding or ionic or other forces, there will generally be sufficient lengths of DNA available for hybridization to oligonucleotides and for amplification.

In cases where the solid support requires elution of the nucleic acid, this may readily be achieved using techniques known in the art, for example by heating, e.g. to 65° C. for 5 to 10 minutes, following which the support may be removed from the medium leaving the nucleic acid in solution. In one embodiment, such heating is automatically obtained in PCR by the DNA denaturation step preceding the cycling program.

In some embodiments, it is desirable to remove RNA from DNA. This may be achieved by destroying the RNA before the DNA separation step, for example by addition of an RNAase or an alkali such as NaOH.

An advantage of the present invention is that it is quick and simple to perform, and with an appropriate combination of cell lysis and nucleic acid binding steps, provides a method that reliably and simply yields isolated nucleic acid in a short period of time, in many cases, less than ten minutes. The simplicity of the method allows for high throughput of samples as well as for Point of Care (POC) applications. The present invention has particular utility as a preliminary first step to prepare nucleic acid for use in nucleic acid-based detection procedures in POC applications.

The invention is advantageously amenable to automation, particularly if particles (especially latex or magnetic particles) are used as the support.

Another aspect of the invention provides a method for detecting the presence or absence of a target cell in a sample, said method comprising:
(a) binding cells in said sample to a solid support to isolate cells from the sample;
(b) lysing the isolated cells;
(c) binding nucleic acid released from said lysed cells to said solid support wherein the solid support comprises antibiotics; and
(d) detecting the presence or absence of nucleic acid characteristic of said target cells within said bound nucleic acid.

In one embodiment, the bound nucleic acid is optionally eluted or removed from the support prior to carrying out the detection step. Whether or not the nucleic acid is eluted may also depend on the particular method used in the nucleic acid binding step. Thus, certain nucleic acid-binding procedures will bind the nucleic acid more tightly than others. In the case of DNA-binding using antibiotic capture, the nucleic acid will elute from the solid support when an elution buffer or other appropriate medium is introduced.

The support-bound nucleic acid may be used directly in a nucleic acid based detection procedure, especially if the support is particulate, simply by re-suspending the support in, or adding to the support, a medium appropriate for the detection step.

A number of different techniques for detecting nucleic acids are known and described in the literature and any of these may be used according to the present invention. For example, the nucleic acid may be detected by hybridization to a probe and very many such hybridization protocols have been described (Sambrook et al., 1989, Molecular Cloning: A Laboratory Manual, 2nd Ed. Cold Spring Harbor Press, Cold Spring Harbor, N.Y.). Most commonly, the detection involves an in situ hybridization step, and/or an in vitro amplification step using any of the methods described in the literature for this. Thus, as mentioned, techniques such as LAR, 3SR and the Q-beta-replicase system may be used. However, PCR and its various modifications such as the use of nested primers, will generally be the method of choice (Abramson and Myers, 1993, Current Opinion in Biotechnology, 4: 41-47 for a review of nucleic acid amplification technologies).

Other detection methods may be based on a sequencing approach, for example, the mini-sequencing approach as described by Syvanen and Soderlund, 1990, Genomics, 8: 684-692.

In amplification techniques such as PCR, the heating required in the first step to melt the DNA duplex may also release the bound DNA from the support in the method described herein. Thus, in the case of a subsequent detection step, such as PCR, the support bound nucleic acid may be added directly to the amplification reaction mix, and the nucleic acid will elute in the first step of the detection process. The entire isolated, support-bound nucleic acid sample obtained according to the invention may be used in the detection step, or an aliquot.

In one embodiment, the results of the PCR or other detection step is detected or visualized. Visualization may be by any one of many means, which are well known in the art. Examples include but are not limited to real-time PCR, ligase chain reaction, fluorescence, and hybrid capture colorimetric assays.

The amplified nucleic acid may also be detected, or the result confirmed, by sequencing, using any of the many different sequencing technologies which are now available, e.g. standard sequencing, solid phase sequencing, cyclic sequencing, automatic sequencing and mini-sequencing. This would be relevant to cloning and SNP determination.

EXAMPLES

This invention is further defined by reference to the following non-limiting example(s). It will be apparent to those skilled in the art that many modifications, both to materials and methods, may be practiced without departing from the scope of the current invention.

Example 1: Preparation of Solid Phase Matrix

Gentamicin was coupled to BSA using N-hydroxysuccinimide (NHS) and 1-Ethyla-3-(3-dimethylaminopropyl) carbodiimide hydrochloride (EDC) according to the procedure described by Grabarek and Gergly [Grabarek, Z. and Gergely, J. (1990) Zero-length crosslinking procedure with the use of active esters. *Anal. Biochem.* 185, 131-135; which is incorporated herein by reference in its entirety].

Briefly, BSA at 10 mg/ml was reacted with 0.4 mg EDC (~2 mM) and 1.1 mg of sulfo-NHS (~5 mM) for 1 hour at 25° C. in MES buffer (pH 5) for 30 minutes. The reaction was quenched with the addition of 2-mercaptoethanol [final 20 mM]. Gentamicin (32 mg) was added and allowed to interact for 2 hours at 25° C. The reaction was quenched with hydroxylamine [final concentration 10 mM]. Similar procedures were employed for dihydroxy-streptomycin binding to BSA.

BSA conjugates of antibiotics were immobilized on polystyrene latex particles by passive absorption. Unbound conjugates were removed by washing with Phosphate Buffered Saline [PBS] containing 0.1% Tween 20.

Figure 5:
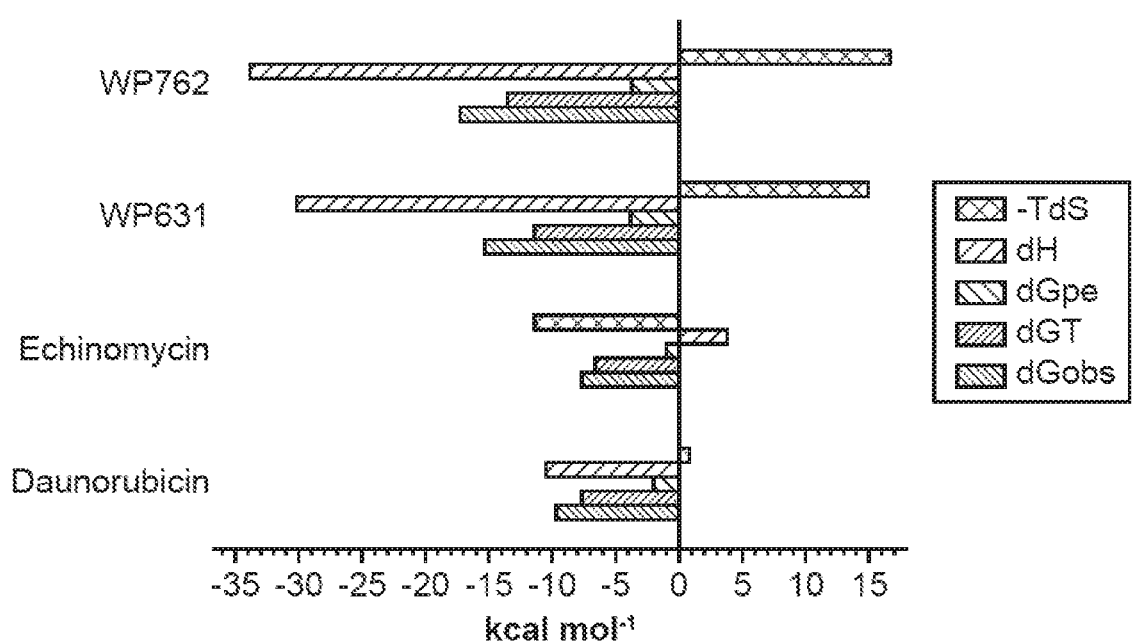
FIG. 5 shows the comparison of the nucleic acid binding thermodynamics for several well characterized intercalating compounds: WP631, WP762, Daunorubicin, and Echinomycin.

DNA samples consisting of the structures shown in FIG. 5 (-Tds, dH, dGpe, dGT, dGobs) were synthesized and the binding thermodynamics for several antibiotics known to bind nucleic acids (WP631, WP762, Daunorubicin, and Echinomycin) were determined.

Example 2: Development of Nucleic Acid Binding Matrices

The feasibility of nucleic acid binding was developed and validated. Unique in-line separation chemistry segregates red blood cells from whole blood in Pad A and collects plasma into a separate zone [Pad B] for further reactions. The whole process is completed in less than one minute. A BoPET/Mylar strip contains reaction pad A, which is impregnated with reagents selected to immobilize RBCs and release plasma to Pad B, which is in conjunction with Pad A. Pad B is incorporated with affinity matrix to bind nucleic acids. Unbound materials will proceed to a sink pad after addition of wash buffer. After optimal incubation time elution buffer is applied and the device closed to transfer the released nucleic acids to Pad D that is part of a second separate BoPET/Mylar strip. Pad D contains the extracted nucleic acids for further processing. Released nucleic acids in Pad D are quantified by standard PCR techniques.

All references cited herein are incorporated by reference in their entireties.

What is claimed is:

1. A device for isolating nucleic acid from a biological sample comprising at least one nucleic acid, the device comprising:
    an affinity matrix comprising at least one nucleic acid binding moiety covalently bound to the affinity matrix, the at least one nucleic acid binding moiety selected from streptomycin and tetracycline, the affinity matrix free of nucleic acid prior to contacting the sample, the affinity matrix configured to non-specifically bind the at least one nucleic acid from the sample in response to contacting the sample, thereby binding the at least one nucleic acid to the affinity matrix; and
    an elution pad configured to retain an elution buffer, the elution buffer configured to elute the at least one nucleic acid from the nucleic acid-bound affinity matrix in response to the elution pad contacting the affinity matrix, thereby isolating the at least one nucleic acid.

2. The device of claim 1, further comprising a sample receiving pad configured to receive the sample comprising the at least one nucleic acid, the sample receiving pad further configured to retain a cell disruption reagent configured to disrupt at least some cells in the sample received by the sample receiving pad, the sample receiving pad further configured to receive a wash buffer, an edge of the sample receiving pad adjoining a first edge of the affinity matrix, the sample receiving pad configured to transport the at least some cells disrupted by the cell disruption reagent via capillary action to the affinity matrix in response to receiving the wash buffer.

3. The device of claim 2, further comprising a sink, an edge of the sink adjoining a second edge of the affinity matrix, the second edge of the affinity matrix opposite to the first edge of the affinity matrix, the sink configured to receive portions of the sample from the affinity matrix not eluted to the elution pad.

4. The device of claim 3, wherein the sink comprises a well.

5. The device of claim 3, wherein the sink comprises a sink pad.

6. The device of claim 3, further comprising a strip, wherein the sample receiving pad, the affinity matrix, and/or the sink are arrayed linearly on the strip.

7. The device of claim 6, further comprising a housing, the housing configured to house the strip, the sample receiving pad, the affinity matrix, the elution pad, and/or the sink.

8. The device of claim 7, wherein a bottom surface of the strip contacts a bottom interior surface of the housing, and where the sample receiving pad, the affinity matrix, and/or the sink are arrayed linearly on the top surface of the strip.

9. The device of claim 8, wherein the strip, the sample receiving pad, the affinity matrix, and/or the sink is removable from the housing.

10. The device of claim 8, further comprising an opening in a top surface of the housing above the receiving pad, thereby providing access to the receiving pad for applying the sample and/or the wash buffer to the receiving pad without opening the housing.

11. The device of claim 10, further comprising a hinged portion of the top surface of the housing, wherein the elution pad is attached to the hinged portion of the top surface of the housing such that the elution pad contacts the affinity matrix when the hinged portion of the top surface of the housing is in a closed position, thereby contacting the elution pad to the affinity matrix when the hinged portion of the top surface of the housing is in the closed position.

12. The device of claim 11, wherein the hinged portion of the top surface of the housing and the elution pad are removable from the housing.

13. The device of claim 1, wherein the at least one nucleic acid binding moiety is streptomycin.

14. The device of claim 1, wherein the at least one nucleic acid binding moiety is tetracycline.

* * * * *